United States Patent
Kiyoura et al.

[11] Patent Number: 5,959,150
[45] Date of Patent: Sep. 28, 1999

[54] PROCESS FOR PREPARING METHYLAMINES

[75] Inventors: Tadamitsu Kiyoura; Shigeki Nakahara, both of Kanagawa-ken, Japan

[73] Assignee: Mitsui Chemicals, Inc., Tokyo, Japan

[21] Appl. No.: 08/426,653

[22] Filed: Apr. 21, 1995

[30] Foreign Application Priority Data

May 11, 1994 [JP] Japan ................................. 6-097168

[51] Int. Cl.$^6$ ................................................. C07C 209/16
[52] U.S. Cl. ........................................................... 564/479
[58] Field of Search ............................................. 564/479

[56] References Cited

U.S. PATENT DOCUMENTS

| | | | |
|---|---|---|---|
| 3,384,667 | 5/1968 | Hamilton | 260/585 |
| 4,398,041 | 8/1983 | Cochran et al. | 564/479 |
| 4,485,261 | 11/1984 | Ashina et al. | 564/479 |
| 4,578,516 | 3/1986 | Ashina et al. | 564/479 |
| 4,582,936 | 4/1986 | Ashina et al. | 564/479 |
| 4,683,334 | 7/1987 | Bergna et al. | 564/474 |
| 4,939,301 | 7/1990 | Grice et al. | 564/477 |
| 5,137,854 | 8/1992 | Segawa et al. | 502/64 |
| 5,210,308 | 5/1993 | Segawa et al. | 564/479 |
| 5,382,696 | 1/1995 | Kiyoura et al. | 564/479 |
| 5,399,769 | 3/1995 | Wilhelm et al. | 564/480 |
| 5,488,165 | 1/1996 | Hutchin et al. | 564/479 |

FOREIGN PATENT DOCUMENTS

| | | |
|---|---|---|
| 0025693 | 3/1981 | European Pat. Off. . |
| 0196965 | 10/1986 | European Pat. Off. . |
| 0593086 | 4/1994 | European Pat. Off. . |
| 4105188 | 8/1991 | Germany . |
| 56-46846 | 4/1981 | Japan . |
| 56-113747 | 9/1981 | Japan . |
| 57-169444 | 10/1982 | Japan . |
| 58-49340 | 3/1983 | Japan . |
| 58-69846 | 4/1983 | Japan . |
| 2-734 | 1/1990 | Japan . |
| 2-27335 | 6/1990 | Japan . |

*Primary Examiner*—Brian M. Burn
*Attorney, Agent, or Firm*—Burns, Doane, Swecker & Mathis, L.L.P.

[57] ABSTRACT

A process for preparing methylamines is disclosed herein which comprises the step of reacting methanol with ammonia in the presence of a mordenite in which the ratio of the length of mordenite crystals in a c axis direction to that of the mordenite crystals in an a axis direction or a b axis direction, c/a or c/b is 2 or more, whereby the synthetic activity of the methylamines can be maintained at a high level, and the production ratio of trimethylamine can be inhibited to a low level of about several percent to predominantly produce dimethylamine and monomethylamine.

18 Claims, 1 Drawing Sheet

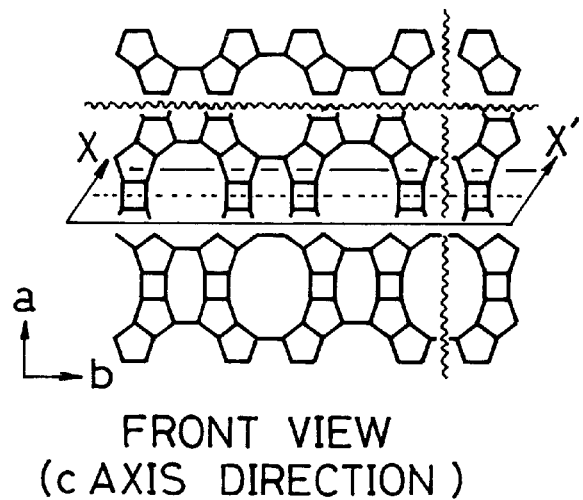
FRONT VIEW
(c AXIS DIRECTION)
F I G. 1 (a)
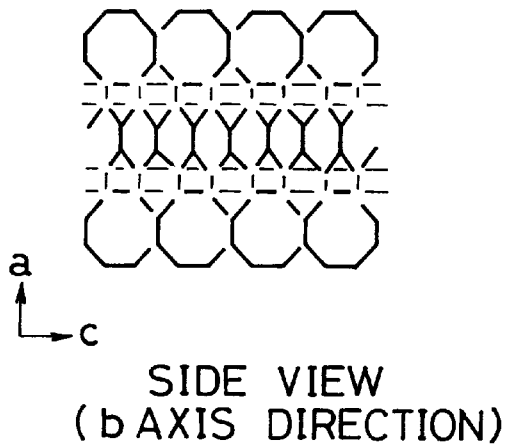
SIDE VIEW
(b AXIS DIRECTION)
F I G. 1 (b)
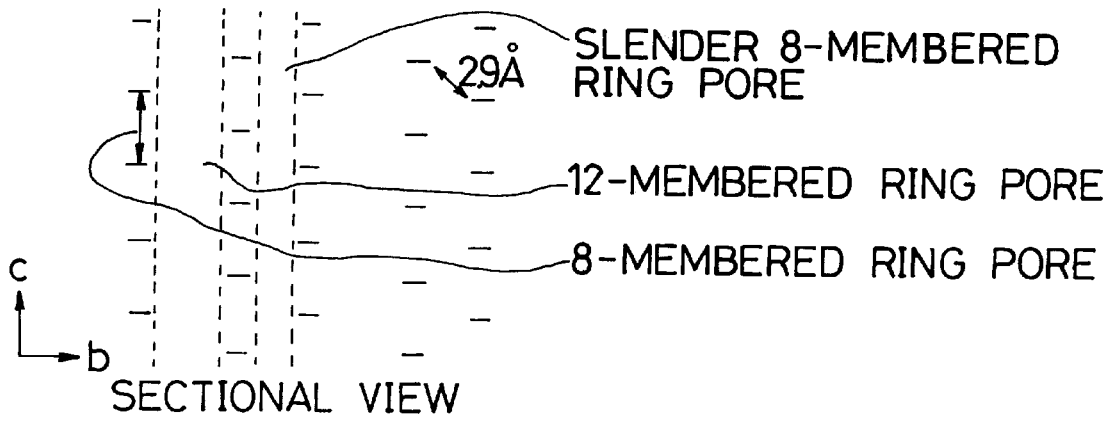
SECTIONAL VIEW
F I G. 1 (c)

PROCESS FOR PREPARING METHYLAMINES

BACKGROUND OF THE INVENTION

1. Field of the Invention

The present invention relates to a process for preparing amines. More specifically, it relates to a process for preparing methylamines from methanol and ammonia by which monomethylamine and dimethylamine are obtained in larger amounts than trimethylamine. Still more specifically, it relates to a crystalline morphology of a mordenite for exerting a more excellent catalytic performance among mordenite catalysts which can be used to accelerate the reaction of methanol with ammonia. The methylamines which can be obtained by the present invention are useful compounds applicable to many uses as materials for the manufacture of various kinds of solvents and intermediates for synthetic organic synthetic compounds.

2. Description of the Related Art

Methylamines, i.e., monomethylamine, dimethylamine and trimethylamine can be prepared by a method which comprises reacting methanol or a mixture of methanol and dimethyl ether with ammonia, a method which comprises the catalytic hydrogenation of prussic acid, or the like.

Thus, these methylamines can be produced as a mixture of monomethylamine, dimethylamine and trimethylamine, and they have corresponding uses, respectively. On the other hand, among these methylamines, the demand of dimethylamine and monomethylamine is particularly large, but that of trimethylamine is small under the existing circumstances. In the methylamines obtained by the reaction of methanol with ammonia in the presence of a usual amorphous silica-alumina as a catalyst, trimethylamine is a main component, and the yield of dimethylamine whose demand is large is inconveniently low. It has been disclosed that in order to overcome this disadvantage, a dehydrated crystalline aluminosilicate (zeolite) having a pore diameter of from 5 to 10 Å can be used in the reaction of an alcohol having 1 to 18 carbon atoms with ammonia, and in this case, the production of the monoamine and diamine predominates over that of the triamine. Furthermore, it has also been disclosed that natural zeolites and synthetic zeolites are mentioned as some kinds of zeolites suitable for the above-mentioned reaction. It has further been disclosed that suitable examples of the natural zeolite include faujasite, analcime, clinoptilolite, ferrierite, chabazite, gmelinite, levynite, erionite and mordenite, and suitable examples of the synthetic zeolite include X type, Y type and A type (U.S. Pat. No. 3,384,667, 1968).

There have also been disclosed a method which comprises mixing methanol with ammonia in a specific ratio, and then reacting them in the presence of a catalyst such as a mordenite to obtain monomethylamine in a particularly large amount (Japanese Patent Application Laid-open No. 113747/1981), and another method in which monomethylamine is disproportionated by a crystalline aluminosilicate selected from sodium ion type mordenites to selectively obtain a large amount of dimethylamine (Japanese Patent Application Laid-open No. 46846/1981).

Disclosed have also been a method in which a natural mineral is used as the mordenite in about the same manner as in the above-mentioned U.S. Pat. No. 3,384,667 (Japanese Patent Application Laid-open No. 169444/1982), a method using, as the catalyst, a mordenite subjected to ion exchange with lanthanum ions (Japanese Patent Application Laid-open No. 49340/1983), a method using, as the catalyst, a mordenite in which the amount of ion-exchanged alkaline metal ions is limited to a specific range (Japanese Patent Application Laid-open No. 210050/1984 and U.S. Pat. No. 4,578,516), a method using a steam-treated mordenite as the catalyst (Japanese Patent Application Laid-open No. 227841/1984 and U.S. Pat. No. 4,582,936), a method using an A type zeolite containing a small amount of a binder as the catalyst (Japanese Patent Application Laid-open No. 69846/1983), and a method using a Rho type (ZK-5) zeolite as the catalyst.

When the zeolite catalyst is used in the above-mentioned manner, the production of trimethylamine can be inhibited, but there is also known a method in which for the purpose of bringing the production of trimethylamine into zero or substantially zero, a mordenite having pores modified by a CVD (chemical vapor deposition) of silicon tetrachloride is used as the catalyst [Japanese Patent Application Laid-open No. 262540/1991; J. Catal., Vol. 131, p. 482 (1991); and U.S. Pat. No. 5,137,854].

Another method has also been present in which a chabazite, an erionite, a ZK-5 or a Rho type zeolite modified by precipitating a compound of silicon, aluminum, phosphorus or boron thereon is used as the catalyst to decrease the production of trimethylamine (Japanese Patent Application Laid-open No. 254256/1986 and U.S. Pat. No. 4,683,334). Furthermore, there is also known a method in which an alcohol is reacted with ammonia in the presence of SAPO of a non-zeolite molecular sieve as the catalyst to obtain an alkylamine (Japanese Patent Application Laid-open No. 734/1990).

As described above, by using various kinds of heretofore disclosed zeolite catalysts in the reaction of methanol with ammonia, the production of trimethylamine which is in small demand can be inhibited, and that of dimethylamine which is in large demand can be increased. It is well known from old days that among the zeolites usable for this purpose, the mordenites are particularly excellent in activity for the synthesis of the methylamines [U.S. Pat. No. 3,384,667, 1968; and J. Catal., Vol. 82, p. 313 (1983)]. However, in the case that the mordenites employed are those prepared by a hydrothermal synthesis method or the natural mordenites, the activity for the synthesis of the methylamines and the performance for the production inhibition of trimethylamine are fairly different among these kinds of mordenites, even if a mordenite content, an impurity content, a cation composition and the like are substantially similar and even if values obtained by a standard powder X-ray diffraction and pore diameters obtained from the adsorption isotherm of argon at a liquid argon temperature are at similar levels. This difference is not so large in the case of the synthetic mordenites, but it is particularly noticeable in the case of the natural mordenites.

U.S. Pat. No. 3,384,667 (1968) has suggested that zeolites having a pore diameter of from 5 to 10 Å are used in order to predominantly obtain a monoalkylamine and a dialkylamine from an alcohol having 1 to 15 carbon atoms and ammonia, and as one of these zeolites, a natural mordenite is suitable. However, it is not disclosed at all which kind of natural mordenite is suitable. In Japanese Patent Publication No. 27335/1990, it is described that in preparing the methylamines from methanol and ammonia, a natural mordenite having an effective pore diameter of from 1 to 5 Å is suitable as the catalyst, but a more detailed description is not disclosed at all therein. That is to say, with regard to characteristics of the mordenites, particularly the natural mordenites suitable for the manufacture of the methylamines from methanol and ammonia, any standards for selection have not been established, and it has been difficult to prepare the catalyst for efficiently accelerating the reaction, while sufficiently inhibiting the production of trimethylamine.

SUMMARY OF THE INVENTION

An object of the present invention is to provide a method for preparing methylamines in the presence of a mordenite as a catalyst having a crystalline morphology particularly suitable for the preparation of the methylamines without the above-mentioned problems, i.e., the industrial preparation of the methylamines in which the production of dimethylamine and monomethylamine is increased and that of trimethylamine is sufficiently inhibited.

The present inventors have conducted intensive research regarding a method for industrially preparing the methylamines in the presence of a mordenite as a catalyst so as to inhibit the production of trimethylamine to an extremely low level and to increase the production of dimethylamine. As a result, it has been found that when there is used, as a starting material of the catalyst, a mordenite in which the ratio of the length of the crystal of the mordenite used as the catalyst in a c axis direction to that of the crystal in an a axis direction or a b axis direction, c/a or c/b is 2 or more, more preferably 3 or more, the production of trimethylamine can be inhibited to a sufficiently low level and the methylamines can be efficiently prepared. In consequence, the present invention has now been completed.

That is to say, the present invention is directed to a process for preparing methylamines which comprises the step of reacting methanol or methanol and dimethyl ether with ammonia in the presence of a mordenite in which the ratio of the length of a mordenite crystal in a c axis direction to that of the mordenite crystal in an a axis direction or a b axis direction, c/a or c/b is 2 or more.

When the mordenite in which the ratio of the length of the mordenite crystal in the c axis direction to that of the mordenite crystal in the a axis direction or the b axis direction, c/a or c/b is 2 or more is used as the catalyst or a starting material for the preparation of the catalyst in manufacturing the methylamines by the reaction of methanol with ammonia, the synthetic activity of the methylamines can be maintained at a high level and the production ratio of trimethylamine can be decreased to a low level of few percent, whereby a step can be omitted in which trimethylamine is recycled through a reaction system to disproportionate trimethylamine, with the result that the process for preparing the methylamines can be simplified and the amount of utilities to be used can be decreased. Hence, it is apparent that the process for preparing the methylamines of the present invention is industrially advantageous.

BRIEF DESCRIPTION OF THE DRAWING

FIG. 1 illustratively shows the crystalline structure of a mordenite, and

FIG. 1 (*a*) is a front view in a c axis direction,

FIG. 1 (*b*) is a side view in a b axis direction, and

FIG. 1 (*c*) is a sectional view cut along the line X—X' in FIG. 1 (*a*).

DETAILED DESCRIPTION OF THE PREFERRED EMBODIMENTS

A conventional mordenite which has often been used in the synthetic reaction of methylamines is a crystalline aluminosilicate represented by $Na_8(Al_8Si_{40}O_{96})24H_2O$ (Atlas of Zeolite Structure Types, W. M. Meier and D. H. Olson, 1987, Butter worths). Alternatively, the mordenite may be represented by $Me_{1/n}(AlSi_5O_{12})3H_2O$ (Me is an n-valent alkali metal atom, an alkaline earth metal atom or a hydrogen atom) (Japanese Patent Laid-open Nos. 169444/1982 and 210050/1984 and the like).

In either case, the Si/Al ratio and the silica/alumina ratio $(SiO_2/Al_2O_3)$ of the conventional mordenite is about 5 and 10, respectively, irrespective of the natural mordenite or the synthetic mordenite (Zeolon made by Norton Co., Ltd, LZM-8 made by UCC, CM-180 made by La Grande Paroisse Co., Ltd. or the like). The mordenites having such a silica/alumina ratio as to be far over 11 are not known except special synthetic products.

Thus, the mordenite which can be used in the process of the present invention has a silica/alumina ratio of 10 or more. If a silica/alumina ratio of about 10 is necessary, the conventional synthetic or natural mordenite can be used. If a silica/alumina ratio of 11 or more is necessary, the mordenite can be subjected to a usual treatment such as an acid treatment or a steam treatment. Alternatively, the mordenite having such a silica/alumina ratio can be prepared by obtaining a gel-like slurry having a composition of

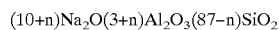

$$(10+n)Na_2O(3+n)Al_2O_3(87-n)SiO_2$$

(wherein n is from 0 to 4) from an aqueous sodium silicate solution and an aqueous aluminum chloride solution, and then subjecting the slurry to hydrothermal synthesis at 130 to 250° C. for 10 hours to several days [Am. Mineral, Vol. 65, p. 1012 (1972)].

In the structure of the mordenite by X-ray diffractometry, as shown in FIG. 1, a wide 12-membered ring pore (a maximum pore size=6.5–7.0 Å) and a longitudinally slender 8-membered ring pore are arranged in parallel with a c axis direction, and these pores are connected to the 8-membered ring pores in a b axis direction. In an a axis direction, no pores are observed, and thus in a surface vertical to the a axis, the pores are not opened. Furthermore, in the a axis and b axis directions, bonds are fewest at the position indicated by a wave line in the front view of FIG. 1, and so cleavage easily occurs at this position. According to the observation of the side view of FIG. 1, any surface on which the cleavage particularly easily occurs is not present in the c axis direction.

In the process of the present invention, as a catalyst or a starting material of the catalyst, there can be used the mordenite, particularly the natural mordenite having the above-mentioned mordenite crystal morphology in which the ratio of the length of the mordenite crystal in the c axis direction to that of the mordenite crystal in the a axis direction or the b axis direction, c/a or c/b is 2 or more, preferably 3 or more. The value of c/a or c/b can usually easily be known by observing an enlarged image of from 200,000 to 1,000,000 times of a mordenite sample through an electron microscope. A mordenite having the axially long cylindrical crystals corresponds to the above-mentioned mordenite. It can be clearly known by observing an electron diffraction pattern in situ which part of the crystals observed by the electron microscope corresponds to the c axis. Alternatively, the value of c/a or c/b can also easily be judged from the image of the mordenite sample enlarged 400 to 2,000 times by a scanning electron microscope (SEM). In particular, the natural mordenite in which long fibrous crystals are observed by SEM (the value of c/a or c/b is extremely large) is particularly preferable as the starting material of the catalyst.

Most morphologies of the mordenite crystals in which the value of c/a or c/b is less than 2 are from spherical to elliptical, rectangularly parallelepipedic and cylindrical having short axis. If the mordenite having such a crystalline morphology is used as the starting material of the catalyst, it is difficult to prepare the preferable catalyst.

All of the crystalline morphologies confirmed by the observation are not required to have a c/a or c/b ratio of 2 or more. If the reaction of methanol with ammonia is carried out in the presence of the catalyst obtained by using the mordenite containing that having a c/a or c/b ratio of 2 or more, preferably 3 or more as the starting material, the production of trimethylamine can be sufficiently inhibited with a high conversion of methanol. In the crystalline morphologies, the ratio of the crystalline morphology having a c/a or c/b ratio of 2 or more, preferably 3 or more is preferably 30% or more, more preferably 40% or more. Usually in most cases, the length of the a axis or the b axis of the mordenite crystals which can be used in the process of the present invention is in the range of from about 20 to 1000 nm, and the length of the c axis is in the range of from about 40 to 100,000 nm. In general, the hydrogen ion type mordenite is often used because of exerting a high activity, but the mordenite in which part of the hydrogen ions are replaced with a small amount of alkali metal ions or alkaline earth metal ions can also be used. The synthetic or the natural mordenite can be obtained in the form of an alkali metal ion type, and so the hydrogen ion type mordenite can be prepared by thermal decomposition after ion exchange with ammonium ions. Alternatively, the alkali metal ion type mordenite may be treated with a 1 to 3N mineral acid to obtain the hydrogen ion type which is a precursor of the catalyst.

The natural mordenite is a mixture of a mordenite component and other components. In the mordenite which is often used, the amount of alkali metals and alkaline earth metals is substantially zero in the mordenite component. In general, the amount of these metals is preferably in the range of from 0.1 to 1%. In the mordenite which is often used, the amounts of sodium, potassium and the total of calcium and magnesium present in feldspars and clays which are components other than the mordenite are in the range of from about 0.2 to 0.5%, about 0.2 to 5% and about 0.2 to 5%, respectively. The content of the alkali metals and the alkaline earth metals in the mordenite component and the other components can be measured separately in the mordenite, in the clays and in the feldspars by means of an analytical electron microscope.

The sodium ions in the mordenite can be substantially completely replaced with hydrogen ions by the above-mentioned ion exchange treatment. The amount of the remaining sodium ions is in the range of from about 0.1 to 0.2%, but potassium ions, calcium ions and magnesium ions remain in some amount on occasion. Even if the amount of these remaining substances fluctuates, the activity and the trimethylamine production inhibiting performance of the finally obtained catalyst are scarcely affected. In addition, quartz, the feldspars, the amorphous clays and the like which might be contained as impurities in the catalyst have little influence on the performance of the finally obtained catalyst. A mordenite content in the natural mordenite which is often used is in the range of from about 40 to 80%, and the catalyst finally obtained from this natural mordenite has a satisfactory performance.

Even if the mordenite content is less than 40%, the synthetic reaction of the methylamines can proceed, but the space time yield of the catalyst deteriorates and the volume of a reaction vessel required to from a unit amount of the product increases, which is economically inconvenient. In general, a catalyst having a mordenite content of 40% or more can be used.

The mordenite converted from the alkali metal ion type into the hydrogen ion type usually has a high activity but is insufficient in the performance of inhibiting the production of trimethylamine. Also with regard to the mordenite which remains converted into the hydrogen ion type, the production ratio of trimethylamine is largely different between the mordenite having a c/a or c/b ratio of 2 or more and the mordenite having a c/a or c/b ratio of less than 2, the above-mentioned c/a or c/b ratio being the feature of the present invention. Even in this case, the difference of a pore diameter is not substantially observed between both the mordenites. As a technique for sufficiently imparting the trimethylamine production inhibiting performance to the mordenite, there can be used one or a combination of two or more of a method in which the ion exchange of a suitable cation is carried out, a method in which an outer surface is subjected to a dealuminumation treatment, a method in which a treatment is carried out by the use of high-temperature and high-pressure steam, and a method in which an outer surface is subjected to a silylation treatment.

Examples of the cation suitable for the above-mentioned purpose include sodium ions, magnesium ions, and ions of a rare earth element-such as lanthanum. In a typical example, the concentration of sodium ions is first regulated to be in the range of from 0.3 to 1% by weight by ion exchange (U.S. Pat. No. 4,578,516), and the obtained mordenite is then treated with water vapor at 300 to 500° C. under atmospheric pressure to 30 kg/cm$^2$G for an interval of several hours to 100 hours (U.S. Pat. No. 4,582,936) to obtain a catalyst which can inhibit the production of trimethylamine to about 5 to 10%.

Methods using the catalyst in which the magnesium ions or the ions of a rare earth element such as lanthanum are ion-exchanged are described in detail in Japanese Patent Application Laid-open No. 49340/1983 and J. Catal., Vol. 82, p. 313 (1983). The catalyst obtained by the ion exchange of the magnesium ions or the ions of a rare earth element such as lanthanum can be further treated with the steam to further increase the inhibition effect of the production of trimethylamine.

If the catalyst is brought into contact with an amine compound prior to the high-temperature and high-pressure steam treatment, the inhibition effect of the trimethylamine production can be further increased. This method is described in U.S. Pat. No. 5,382,696.

A treatment technique suitable to obtain the catalyst by which the production of trimethylamine can be suppressed to about several percent is a method in which the outer surface of the mordenite is subjected to silylation with a suitable silylating agent. The size of the molecule of the silylating agent to be used is larger than the diameter of the pores in the mordenite, and therefore the only outer surface of the mordenite is selectively silylated. No particular restriction is put on the treatment method with the silylating agent, but there can be used a treatment in a gaseous phase by CVD (chemical vapor deposition) and a treatment in a liquid phase in which the silylating agent is dissolved in a suitable solvent. In order to manufacture a great deal of the catalyst, the method of the liquid phase treatment is often employed.

One example of the preferable silylation treatment method in the liquid phase will be described. Prior to the treatment of the mordenite with the silylating agent in the liquid phase, the moisture content in the pores of the mordenite is regulated to a predetermined level. The moisture content in the mordenite is preferably in the range of from 3 to 40% by weight, more preferably 4 to 30% by weight. If the moisture content is outside the above-mentioned range, it is difficult to obtain the silylated catalyst by which the production of trimethylamine can be maintained at a low value of about 1%. The regulation of the moisture content in the mordenite can be carried out by various techniques, and for example, the following method is convenient. The mordenite which has undergone the ion exchange into the hydrogen ion type, deionized water washing, filtration and drying is calcined at 400 to 600° C. to once bring the moisture content in the pores of the mordenite into substantially zero. Next, the mordenite is allowed to adsorb the moisture of water having a saturated vapor pressure at about 0 to 50° C., so that a moisture content of from 3 to 40% by weight is given to the mordenite. In the case of a laboratory scale, the mordenite is placed in the upper part of a desiccator containing water in its lower part, and it is then allowed to stand at room temperature for 10 to 30 hours, whereby a moisture content of from 5 to 20% by weight can be given to the mordenite. As another method for giving a predetermined moisture content to the mordenite, the mordenite may be treated with an aqueous acid solution to convert the same into the hydrogen ion type, and the thus treated mordenite may be air-dried, and then dried at 100 to 160° C., whereby a moisture content of from 3 to 30% by weight can be given to the mordenite. According to this method, a trace amount of the acid is occluded together with moisture in the pores of the mordenite, and the acid can conveniently perform a catalytic function. That is to say, the acid slowly diffuses into the surface of the mordenite to smoothly advance the silylation reaction.

Examples of the silylating agent which can be used in the silylation treatment include alkoxides of silicon such as tetramethoxysilane and tetraethoxysilane, silicon tetrachloride, dimethyl dichlorosilane, trimethyl chlorosilane, tetramethyl disilazane and hexamethyl disilazane.

The liquid phase silylation treatment of the mordenite is usually carried out by dissolving the silylating agent in a suitable solvent. Examples of the solvent include aliphatic and alicyclic hydrocarbons such as hexane, octane and cyclohexane and aromatic hydrocarbons such as benzene, toluene and xylene. It is preferable to select the suitable solvent in compliance with the used silylating agent.

The amount of the silylating agent is usually in the range of from 1 to 10% to the employed mordenite in terms of silicon dioxide as a silicon content in the silylating agent. The concentration of the silylating agent in the solvent is usually in the range of from 2 to 30% by weight. If a moisture content in the solvent which can be used in the silylation treatment is high, the silylating agent is hydrolyzed and it is consumed in vain. Thus, the moisture content in the solvent for use in the silylation treatment is preferably low.

The mordenite is dispersed in the solution of the above-mentioned silylating agent, whereby a silicon compound is deposited and fixed on the mordenite.

The temperature at which the silylation treatment is carried out is from room temperature to the boiling point of the solution, and it is usually in the range of from 20 to 200° C. When the treatment is done under pressure, the treatment temperature can be further raised.

The time required for the silylation treatment depends mainly upon the treatment temperature and the like. When a treatment temperature in the vicinity of room temperature is used, the treatment time is usually in the range of from 3 to 30 hours, and when a treatment temperature of from 60 to 90° C. is used, the treatment time is usually in the range of from 1 to 10 hours.

The mordenite which has just been treated is separated from the treatment solution by a usual technique such as filtration or centrifugal separation, and then heated under the atmosphere of an inert gas such as nitrogen or heated under reduced pressure to remove the organic solvent which adheres to the mordenite or which is adsorbed by the mordenite. Next, the mordenite is subjected to a heat treatment (calcination) at 300 to 600° C. under an atmosphere of nitrogen, air or oxygen to obtain the catalyst. If the mordenite which is the starting material is already molded into grains or tablets, it can be directly used as the catalyst. If the mordenite is in the form of powder, it is extruded in a conventional manner or molded into tablets, thereby obtaining the catalyst.

The amount of $SiO_2$ formed by the silylation treatment followed by the calcination is preferably in the range of from 1 to 10% by weight, more preferably 1 to 8% by weight based on the weight of the catalyst. This value depends upon the outer surface area of the mordenite to be used, and therefore it is preferable to experimentally decide the optimum value.

The raw materials which can be used in the method of the present invention are methanol or a mixture of methanol and dimethyl ether and ammonia. In addition, a methylamine such as monomethylamine may be mixed with the reaction materials. With regard to the molar ratio of ammonia to methanol or the like, the mols of ammonia per mol of methanol or the like are 0.5 or more, preferably in the range of from 1 to 5, but in general, it is often in the range of from 1 to 3.

The flow rate of a reaction gas which is fed to a catalyst layer is in the range of from 200 to 5000 liters/hr./liter of the catalyst in terms of SV, and a reaction pressure is in the range of from 1 to 40 $kg/cm^2G$, preferably 10 to 30 $kg/cm^2G$. In the practice of the reaction, a catalyst layer temperature is in the range of from 250 to 450° C., preferably 270 to 360° C.

A reactor which can be used to practice the method of the present invention is a usual fixed bed or a fluidized bed reactor.

From a gas at the outlet of the reactor, methylamines are isolated and collected by a separation-purification device. However, in the method of the present invention, the production of trimethylamine is about several percent, and therefore the separation step of trimethylamine can be simplified and a step for recycling trimethylamine through a reaction system is unnecessary. Thus, the whole manufacturing process can be simplified.

Now, the present invention will be described in more detail with reference to examples and comparative examples, but the scope of the present invention should not be limited to these examples.

EXAMPLE 1

A natural mordenite obtained in Oga, Akita Prefecture, Japan was used as a starting material for a catalyst to prepare the catalyst. With regard to this natural mordenite, when it was observed at a magnification of 200,000 times through an electron microscope, the length of the c axis of mordenite crystals was in the range of from 300 to 400 nm and the length of the a axis or the b axis of the mordenite crystals was in the range of from 100 to 150 nm, and thus the ratio of c/a or c/b was in the range of from 2 to 4. The pore diameter of the mordenite calculated on the basis of the adsorption of argon at a liquid argon temperature was 6.2 Å.

Afterward, 110 g of the natural mordenite (a mordenite content=about 65%) having a granule diameter of from 2 to 3 mm was poured into 1 liter of 2N hydrochloric acid, followed by shaking at 35° C. for 10 hours. The mordenite was collected by filtration and then poured into 1 liter of fresh 2N hydrochloric acid, followed by shaking at 35° C. for 10 hours again. Next, the mordenite was collected by filtration, air-dried, and then dried at 140° C. to obtain the mordenite having pores in which 9% of moisture and a trace amount of hydrochloric acid were occluded. The thus obtained mordenite was of a substantially complete hydrogen ion type and had an Na content of 0.14%.

Into 100 g of a toluene solution in which 4.5 g of tetraethoxysilane was dissolved, 50 g of the above-mentioned hydrogen ion type mordenite was added, and the mixture was then shaken at room temperature (20–25° C.) for 10 hours. Afterward, the mordenite was collected by filtration, heated at 300° C. for 2 hours in a nitrogen gas flow, and then further heated 500° C. for 4 hours in an air flow. The resultant granular mordenite was directly used as a catalyst for a reaction. The degree of silylation on the catalyst corresponded to 2.5% by weight based on the catalyst in terms of $SiO_2$.

Next, a stainless steel reaction tube having an inner diameter of 1 inch was filled with 40 g (60 ml) of the above-mentioned catalyst, and the reaction tube was then heated from the outside in a sand fluidized bath.

Methanol and ammonia were fed at flow rates of 20 g/hr and 21 g/hr, respectively, to the reaction tube under pressure via an evaporator, and the reaction was then carried out at 300° C. under a pressure of 19 kg/cm$^2$G.

After 130 hours had elapsed since the start of the reaction, gas at the outlet of the reaction tube was analyzed. As a result, it was found that the conversion of methanol was 93%, the selectivities of monomethylamine, dimethylamine and trimethylamine were 34.8%, 63.1% and 2.1%, respectively.

COMPARATIVE EXAMPLE 1

A natural mordenite obtained in Kawarago, Miyagi Prefecture, Japan was used as a starting material for a catalyst to prepare the catalyst. With regard to the crystalline morphology of this natural mordenite, when it was observed at a magnification of 200,000 times through an electron microscope, the ratio of the length of the c axis of mordenite crystals to the length of the a axis or the b axis of the mordenite crystals was in the range of from 1 to 1.5. The amount and composition of quartz, feldspars, amorphous clays which were the impurities of the natural mordenite were of the same level as in the starting material of Example 1. The pore diameter of the mordenite calculated on the basis of the adsorption of argon at a liquid argon temperature was 6.0 Å.

Next, 110 g of the natural mordenite (a mordenite content=about 68%) having a particle diameter of from 2 to 3 mm was added into 1 liter of 2N hydrochloric acid, followed by shaking at 35° C. for 10 hours. Afterward, the mordenite was separated, and 1 liter of fresh 2N hydrochloric acid was then added to the separated mordenite, followed by a similar treatment for 10 hours. Next, the mordenite was collected by filtration, air-dried, and then dried at 140° C. to obtain the mordenite having pores in which 9% of moisture and a trace amount of hydrochloric acid were occluded. In the thus obtained mordenite, an Na content was 0.13%, and the amount of the other remaining cations was about the same as in Example 1. Into 100 g of a toluene solution containing 4.5 g of tetraethoxysilane, 50 g of the obtained mordenite was thrown, and the mixture was then shaken at room temperature for 10 hours. Afterward, the mordenite was collected by filtration, heated at 300° C. for 2 hours in a nitrogen gas flow, and then further heated 500° C. for 4 hours in an air flow to prepare the catalyst. The degree of silylation was 2.6% by weight based on the catalyst in terms of $SiO_2$.

Next, the same reaction tube as in Example 1 was filled with 40 g of the above-mentioned catalyst, and the synthesis of methylamines was tested under the same reaction conditions as in Example 1. After 130 hours had elapsed since the start of the reaction, gas at the outlet of the reaction tube was analyzed. As a result, it was found that the conversion of methanol was 88%, the selectivities of monomethylamine, dimethylamine and trimethylamine were 35.2%, 58.5% and 6.3%, respectively.

That is to say, when the methylamines are synthesized by the use of the catalyst prepared by employing, as the starting material, the mordenite having the crystalline morphology in which the ratio of c/a or c/b is less than 2, the conversion of methanol is lower and the amount of trimethylamine formed as a by-product is larger, as compared with a case where the mordenite having a c/a or c/b ratio of 2 or more is used as the starting material. In consequence, it is apparent that the employment of the mordenite having a c/a or c/b ratio of less than 2 cannot lead to preferable results.

EXAMPLE 2 TO 4

Natural mordenites having c/a or c/b ratios of more than 2 sampled at different points in Itado, Akita Prefecture, Japan were used as starting materials for catalysts and the same procedure as in Example 1 was carried out to prepare the catalysts, and the synthetic reaction of methylamines was tested under the same reaction conditions as in Example 1. The obtained results are shown in Table 1.

COMPARATIVE EXAMPLES 2 AND 3

Various natural mordenites having c/a or c/b ratios of less than 2 were used as starting materials for catalysts and the same procedure as in Example 1 was carried out to prepare the catalysts, and the synthetic reaction of methylamines was tested under the same reaction conditions as in Example 1. The obtained results are shown in Table 1.

TABLE 1

|  | c/a | Mordenite Content (%) | MeOH Conversion (%) |
|---|---|---|---|
| Example 2 | 3–10 | 64 | 92.8 |
| Example 3 | 10–50 | 71 | 91.5 |
| Example 4 | 10–30 | 68 | 93.6 |
| Comp. Ex. 2[a] | 1–1.5 | 72 | 89.1 |
| Comp. Ex. 3[b] | 1–1.5 | 65 | 87.8 |

|  | Selectivity (%) of Methylamines | | |
|---|---|---|---|
|  | Mono-form | Di-form | Tri-form |
| Example 2 | 34.7 | 62.8 | 2.5 |
| Example 3 | 35.1 | 63.0 | 1.9 |
| Example 4 | 35.9 | 61.9 | 2.2 |
| Comp. Ex. 2[a] | 37.0 | 56.5 | 6.5 |
| Comp. Ex. 3[b] | 38.3 | 55.5 | 6.2 |

TABLE 1-continued

Note:
[a]It was sampled in Amagouchi, Shimane Prefecture, Japan.
[b]It was sampled in Tenei, Fukushima Prefecture, Japan.

EXAMPLE 5

A natural mordenite sampled in Kawazu, Shizuoka Prefecture, Japan was used as a starting material for a catalyst to prepare the catalyst. When this natural mordenite was observed at a magnification of 600 times through an SEM, it was apparent that the mordenite had a long fibrous crystal morphology. The c/a or c/b ratio of the mordenite crystals was mainly in the range of from 30 to 500.

The above-mentioned mordenite was crushed, and the resultant particles having a diameter of from 2.5 to 4.0 mm were collected by a sieve. Next, 300 g of the mordenite particles was thrown into 2.5 liters of 3N sulfuric acid, and the mixture was then gently shaken at 30° C. for 10 hours. The solid phase was collected by filtration, and then thrown into 2.5 liters of fresh 3N sulfuric acid, and the mixture was further shaken for 10 hours. The solid phase was collected by filtration, dried at 140° C., and calcined at 600° C. for 5 hours to obtain a hydrogen ion type mordenite. Afterward, 100 g of this hydrogen ion type mordenite was immersed in 400 g of a 0.01N aqueous sodium nitrate solution for 1 minute, and then immediately washed with deionized water to obtain an NaH type mordenite having a sodium content of 0.95% by weight. This mordenite was dried, and then calcined at 600° C. to obtain the catalyst. Next, a stainless steel reactor having an inner diameter of 1 inch was filled with 40 g of this catalyst, and the synthesis of methylamine was carried out for 15 hours under the same conditions as in Example 1 and the reaction was then discontinued. Next, steam at 450° C. and 15 kg/cm$^2$G was caused to flow through a catalyst layer at an SV of 500 for 15 hours, and the synthesis of methylamines was then tested at a reaction temperature of 300° C. under the same reaction conditions as in Example 1. After 150 hours had elapsed since the start of the reaction, gas at the outlet of the reactor was analyzed. As a result, it was found that the conversion of methanol was 92%, the selectivities of monomethylamine, dimethylamine and trimethylamine were 32.4%, 60.5% and 7.1%, respectively.

EXAMPLE 6

In a 0.1N aqueous sulfuric acid solution, 120 g of the hydrogen ion type mordenite prepared in Example 5 was immersed, and after filtration, the mordenite was dried at 140° C. for 6 hours. Next, the mordenite was allowed to stand overnight at room temperature in the air atmosphere, whereby the pores of the mordenite were allowed to occlude a moisture content of about 8%. Consequently, not only the moisture but also a trace amount of sulfuric acid were occluded in the pores of the mordenite.

The mordenite in which the moisture content had been adjusted was thrown into 0.3 liter of a 0.15 mol/liter solution of tetraethoxysilane in toluene, and the mixture was then gently shaken at room temperature for 13 hours to carry out a silylation treatment. Next, the solid phase was collected by filtration, dried at 140° C. under reduced pressure, and calcined at 600° C. for 5 hours under an air atmosphere to obtain a catalyst. The degree of the silylation was 2.2% by weight based on the catalyst in terms of SiO$_2$.

A stainless steel reactor having an inner diameter of 1.5 inches was filled with 100 g of this catalyst, and the reactor was then heated from the outside in a sand fluidized bath. Methanol and ammonia were fed at flow rates of 55 g/hr and 55 g/hr, respectively, to a catalyst layer under pressure via an evaporator, and a reaction was then carried out at 294° C. under a pressure of 19 kg/cm$^2$G. After 150 hours had elapsed since the start of the reaction, gas at the outlet of the reactor was analyzed. As a result, it was apparent that the conversion of methanol was 95%, the selectivities of monomethylamine, dimethylamine and trimethylamine were 35.4%, 63.0% and 2.0%, respectively. The reaction was further continued for 800 hours, and after the reaction, the conversion of methanol was 94%, the selectivities of monomethylamine, dimethylamine and trimethylamine were 35.6%, 62.5% and 1.9%, respectively.

EXAMPLE 7

A part of a hydrogen ion type mordenite prepared in Example 5 was directly used as a catalyst (c/a or a/b=30–500).

The same reactor as in Example 1 was filled with 40 g of the above-mentioned catalyst, and the synthesis reaction of methylamines was then tested under the same reaction conditions as in Example 1. After 100 hours had elapsed since the start of the reaction, gas at the outlet of the reactor was analyzed. As a result, it was found that the conversion of methanol was 96.7%, the selectivities of monomethylamine, dimethylamine and trimethylamine were 24.2%, 48.6% and 27.2%, respectively.

COMPARATIVE EXAMPLE 4

A mordenite (c/a or a/b=1–1.5) used in Comparative Example 1 was treated with 2N hydrochloric acid to convert the same into a hydrogen ion type, and this type mordenite was directly used as a catalyst.

The same reactor as in Example 1 was filled with 40 g of the above-mentioned catalyst, and the synthesis reaction of methylamines was then tested under the same reaction conditions as in Example 1. After 100 hours had elapsed since the start of the reaction, gas at the outlet of the reactor was analyzed. As a result, it was found that the conversion of methanol was 94.9%, the selectivities of monomethylamine, dimethylamine and trimethylamine were 21.4%, 38.6% and 40.0%, respectively.

EXAMPLE 8

A hydrogen ion type mordenite prepared by the same procedure as in Example 5 was immersed in a 0.1N aqueous sodium nitrate solution for 3 minutes, collected by filtration, dried, and then calcined at 500° C. to obtain a catalyst (c/a or a/b=30–500). A sodium content in the catalyst was 0.95% by weight. Next, a glass reaction tube having an inner diameter of 15 mm was filled with 5 g of this catalyst, and it was then heated in an electric furnace. Methanol and ammonia were fed to the reaction tube at flow rates of 2.5 g/hr and 2.5 g/hr, respectively, and a reaction was then carried out at 320° C. under atmospheric pressure. Afterward, gas at the outlet of the reaction tube was analyzed, and as result, it was found that the conversion of methanol was 87%, the selectivities of monomethylamine, dimethylamine and trimethylamine were 36.1%, 51.4% and 12.5%, respectively.

EXAMPLE 9

A hydrogen ion type mordenite prepared by the same procedure as in Example 5 was immersed in a 0.1N aqueous lanthanum nitrate solution for 10 minutes, collected by filtration, dried, and then calcined at 500° C. to obtain a catalyst (c/a or a/b=30–500). A lanthanum content in the catalyst was 2.1% by weight. Next, this catalyst was brought into contact with water vapor at 500° C. under atmospheric pressure at an SV of 500 $hr^{-1}$ for 3 hours to carry out a steam treatment.

A glass reaction tube having an inner diameter of 15 mm was filled with 5 g of this catalyst, and it was then heated in an electric furnace. Methanol and ammonia were fed to the reaction tube at flow rates of 2.5 g/hr and 2.5 g/hr, respectively, and a reaction was then carried out at 320° C. under atmospheric pressure. Afterward, gas at the outlet of the reaction tube was analyzed, and as a result, it was found that the conversion of methanol was 90%, the selectivities of monomethylamine, dimethylamine and trimethylamine were 37.1%, 52.9% and 10.0%, respectively.

EXAMPLE 10

A hydrogen ion type mordenite prepared in Example 5 was brought into contact with water vapor at 500° C. under atmospheric pressure at an SV of 500 $hr^{-1}$ for 3 hours to obtain a catalyst.

A glass reaction tube having an inner diameter of 15 mm was filled with 5 g of this catalyst, and it was then heated in an electric furnace. Methanol and ammonia were fed to the reaction tube at flow rates of 2.5 g/hr and 2.5 g/hr, respectively, and a reaction was then carried out at 320 20 C. under atmospheric pressure. Afterward, gas at the outlet of the reaction tube was analyzed, and as a result, it was found that the conversion of methanol was 91%, the selectivities of monomethylamine, dimethylamine and trimethylamine were 35.9%, 51.0% and 13.1%, respectively.

EXAMPLE 11

A synthetic mordenite (made by Zeocat Corporation) having the crystalline morphology of a needle form and a c/a or c/b ratio of 4–8 was used as a starting material for a catalyst.

The above-mentioned mordenite which had been converted into a hydrogen ion type was calcined at 500° C., and it was then allowed to stand at room temperature in the air, whereby a moisture content of 9% by weight was occluded in the pores of the mordenite. Next, 10 g of the mordenite was thrown into a solution obtained by dissolving 1.0 g of tetraethyl orthosilicate in 9 g of benzene, and silylation was then carried out at room temperature (20–25° C.) for 30 hours, while the mixture was slowly stirred. Afterward, the mordenite was collected by filtration, dried, and calcined at 500° C. to prepare a catalyst. The degree of the silylation on the catalyst was 3% by weight in terms of $SiO_2$.

A glass reaction tube having an inner diameter of 15 mm was filled with 5 g of this catalyst, and it was then heated in an electric furnace to carry out a methylamine synthesis test. That is to say, methanol and ammonia were fed to the reaction tube at flow rates of 2.5 g/hr and 2.5 g/hr, respectively, and a reaction was then carried out at 310° C. under atmospheric pressure. Afterward, gas at the outlet of the reaction tube was analyzed, and as a result, it was found that the conversion of methanol was 91%, the selectivities of monomethylamine, dimethylamine and trimethylamine were 34.5%, 61.9% and 3.6%, respectively.

COMPARATIVE EXAMPLE 5

A synthetic mordenite (made by Toyo Soda Mfg Co., Ltd.) having the crystalline morphology of a globular form and a c/a or c/b ratio of less than 2 was used as a starting material for a catalyst.

The above-mentioned mordenite which had been converted into a hydrogen ion type was calcined at 500° C., and it was then allowed to stand at room temperature in the air atmosphere, whereby a moisture content of 8% by weight was occluded in the pores of the mordenite. Next, 10 g of the mordenite was thrown into a solution obtained by dissolving 1.0 g of tetraethyl orthosilicate in 9 g of benzene, and silylation was then carried out at room temperature (20–25° C.) for 30 hours, while the mixture was slowly stirred. Afterward, the mordenite was collected by filtration, dried, and calcined at 500° C. to prepare the catalyst. The degree of the silylation on the catalyst was 3% by weight in terms of $SiO_2$.

A glass reaction tube having an inner diameter of 15 mm was filled with 5 g of this catalyst, and it was then heated in an electric furnace to carry out a methylamine synthesis test. That is to say, methanol and ammonia were fed to the reaction tube at flow rates of 2.5 g/hr and 2.5 g/hr, respectively, and a reaction was then carried out at 310° C. under atmospheric pressure. Afterward, gas at the outlet of the reaction tube was analyzed, and as a result, it was found that the conversion of methanol was 90%, the selectivities of monomethylamine, dimethylamine and trimethylamine were 32.0%, 58.5% and 9.5%, respectively.

The mordenites used in the examples and the comparative examples are all shown together in Table 2.

TABLE 2

| | Mordenite |
|---|---|
| Example 1 | Oga, Akita Prefecture |
| Comp. Ex. 1 | Kawarago, Miyagi Prefecture |
| Example 2 | Itado, Akita Prefecture (A) |
| Example 3 | Itado, Akita Prefecture (B) |
| Example 4 | Itado, Akita Prefecture (C) |
| Comp. Ex. 2 | Amagouchi, Simane Prefecture |
| Comp. Ex. 3 | Tenei, Fukushima Prefecture |
| Example 5 | Kawazu, Shizuoka Prefecture |
| Example 6 | Kawazu, Shizuoka Prefecture |
| Example 7 | Kawazu, Shizuoka Prefecture |
| Comp. Ex. 4 | Kawarago, Miyagi Prefecture |
| Example 8 | Kawazu, Shizuoka Prefecture |
| Example 9 | Kawazu, Shizuoka Prefecture |
| Example 10 | Kawazu, Shizuoka Prefecture |
| Example 11 | Synthetic mordenite (made by Zeocat Corporation, having crystalline morphology of needle form) |
| Comp. Ex. 5 | Synthetic mordenite (made by Toyo Soda Mfg Co., Ltd., having crystalline morphology of globular form) |

Note: The mordenites in Examples 2 to 4 were sampled at different points in the same district.

What is claimed is:

1. A process for preparing methylamines which comprises the step of reacting methanol or methanol and dimethyl ether with ammonia in the presence of a mordenite in which the ratio of the length of mordenite crystals in a c axis direction to that of the mordenite crystals in an a axis direction or a b axis direction, c/a or c/b is 2 or more.

2. The process for preparing methylamines according to claim 1 wherein the c/a or c/b of the mordenite is 3 or more.

3. The process for preparing methylamines according to claim 1 wherein the outer surface of the mordenite is silylated with a silylating agent.

4. The process for preparing methylamines according to claim 2 wherein the outer surface of the mordenite is silylated with a silylating agent.

5. The process for preparing methylamines according to claim 3 wherein the silylation treatment is carried out in a liquid phase.

6. The process for preparing methylamines according to claim 4 wherein the silylation treatment is carried out in a liquid phase.

7. The process for preparing methylamines according to claim 1 wherein the mordenite is a natural mordenite.

8. The process for preparing methylamines according to claim 2 wherein the mordenite is a natural mordenite.

9. The process for preparing methylamines according to claim 3 wherein the mordenite is a natural mordenite.

10. The process for preparing methylamines according to claim 4 wherein the mordenite is a natural mordenite.

11. The process for preparing methylamines according to claim 5 wherein the mordenite is a natural mordenite.

12. The process for preparing methylamines according to claim 6 wherein the mordenite is a natural mordenite.

13. The process for preparing methylamines according to claim 1 wherein the reaction of methanol with ammonia is carried out at 250 to 450° C. under 1 to 40 kg/cm$^2$G.

14. The process for preparing methylamines according to claim 2 wherein the reaction of methanol with ammonia is carried out at 250 to 450° C. under 1 to 40 kg/cm$^2$G.

15. The process for preparing methylamines according to claim 3 wherein the reaction of methanol with ammonia is carried out at 250 to 450° C. under 1 to 40 kg/cm$^2$G.

16. The process for preparing methylamines according to claim 4 wherein the reaction of methanol with ammonia is carried out at 250 to 450° C. under 1 to 40 kg/cm$^2$G.

17. The process for preparing methylamines according to claim 5 wherein the reaction of methanol with ammonia is carried out at 250 to 450° C. under 1 to 40 kg/cm$^2$G.

18. The process for preparing methylamines according to claim 6 wherein the reaction of methanol with ammonia is carried out at 250 to 450° C. under 1 to 40 kg/cm$^2$G.

* * * * *